United States Patent [19]

Dayer et al.

[11] Patent Number: 5,359,032
[45] Date of Patent: Oct. 25, 1994

[54] INTERKEUKIN-1 INHIBITOR

[75] Inventors: Jean M. Dayer, Geneva; Philippe L. Seckinger, Carouge; Gonzalo J. Mazzei, Geneva; Alan R. Shaw, Geneva, all of Switzerland

[73] Assignee: Biogen Inc., Cambridge, Mass.

[21] Appl. No.: 985,506

[22] Filed: Dec. 1, 1992

Related U.S. Application Data

[63] Continuation of Ser. No. 716,787, Jun. 18, 1991, abandoned, which is a continuation of Ser. No. 435,501, Jun. 30, 1989, abandoned, which is a continuation-in-part of Ser. No. 89,632, Aug. 26, 1987, abandoned.

[51] Int. Cl.$^5$ .................... C07K 15/00; A61K 37/02
[52] U.S. Cl. .................... 530/350; 530/351; 530/413; 530/414; 530/415; 530/416; 530/417
[58] Field of Search ............... 530/350, 351, 413, 414, 530/415, 416, 417; 514/2, 12

[56] References Cited

PUBLICATIONS

Balavoine, J. Clin Investigation, 78:1120–24 (1986).
Rosenstreich, Enstein Q J. Biol Med, Biosis Abst. 87:208860 (1987).
Liao J. Exp Med 159:126–136 (1984).
Arend J. Immunol. 134:3868–75 (1985).
Sandborg Chem. Abst. 106:65645r (1986).
Kemp J. Immunol 137:2245–51 (1986).
Brown Proc. Natl Acad Sci 83: 9119–23 (1986).
P. Seckinger and J.-M. Dayer, "Interleukin-1 Inhibitors", 18th Forum In Immunology, pp. 486–488, (May–Jun. 1987)("Seckinger-4").
Seckinger, et al., "A Partially Purified Urinary IL-1 Inhibitor That Interferes with IL-1 Binding", Lymphokine Res., 6 Abstr. 1111 (1987).
Seckinger et al., "A Urine Inhibitor Of Interleukin 1 Activity Affects Both Interleukin 1α and 1β But Not Tumor Necrosis Factor α", J. Immunol., 139, pp. 1541–1545 (1987).
Seckinger et al., "A Urine Inhibitor of Interleukin 1 Activity That Blocks Ligand Binding", J. Immunol., 137, pp. 1546–1549 (1987).

Primary Examiner—Robert J. Hill, Jr.
Assistant Examiner—Shelly Guest Cermak
Attorney, Agent, or Firm—James F. Haley, Jr.; Leslie A. McDonell; Mary Anne Schofield

[57] ABSTRACT

This invention relates to interleukin inhibitors (IL-1 INHs) that selectively inhibit interleukin 1 activity. The invention also relates to processes for purifying such IL-1 INHs from urine and for producing such IL-1 INHs by hosts transformed with recombinant DNA molecules comprising DNA sequences encoding the inhibitors, and to methods of treatment and compositions characterized by such IL-1 INHs. These methods and agents are useful in immunosuppressive and anti-inflammatory applications and therapies.

12 Claims, 9 Drawing Sheets

DEAE-SEPHAROSE FRACTIONS

AcA54 FRACTIONS

▲ = AcA54, 2nd FILTRATION FRACTION
△ = AcA54, 1st FILTRATION FRACTION
× = DEAE - SEPHAROSE COLUMN FRACTION
● = QAE - SEPHAROSE COLUMN FRACTION
○ = URINARY FRACTION

FIG. 5

IL 1 INH ACTIVITY MEASURED IN THE IL 1/LAF ASSAY

| FINAL CONCENTRATION OF hrIL-1 (pg/ml) TO PHA-STIMULATED THYMOCYTES | FORM OF hrIL-1 ADDED TO THE THYMOCYTES | FINAL DILUTION OF AcA54 INHIBITORY FRACTION[a] | | | |
|---|---|---|---|---|---|
| | | NONE | 1/20 | 1/40 | 1/80 |
| | | [$^3$H]-TdR INCORPORATION IN MURINE THYMOCYTES (cpm) | | | |
| 0 | — | 1.1 ± 0.1 | 1.1 ± 0.2 | 1.3 ± 0.1 | 1.1 ± 0.1 |
| 20 | α | 3.5 ± 0.4 | 1.0 ± 0.1 | 1.1 ± 0.2 | 1.1 ± 0.1 |
| | β | 5.7 ± 0.4 | 1.0 ± 0.1 | 1.1 ± 0.1 | 1.0 ± 0.2 |
| 40 | α | 8.6 ± 3.0 | 1.0 ± 0.1 | 0.9 ± 0.1 | 1.0 ± 0.1 |
| | β | 8.2 ± 2.0 | 1.0 ± 0.1 | 1.2 ± 0.2 | 1.5 ± 0.4 |
| 100 | α | 14.6 ± 1.0 | 1.0 ± 0.1 | 1.4 ± 0.1 | 2.5 ± 0.5 |
| | β | 15.4 ± 2.2 | 1.2 ± 0.1 | 1.6 ± 0.1 | 3.2 ± 0.4 |
| 2000 | α | 24.7 ± 3.5 | 10.2 ± 1.5 | 16.0 ± 3.1 | 25.4 ± 4.7 |
| | β | 20.1 ± 2.6 | 20.1 ± 2.6 | 12.1 ± 4.0 | 22.8 ± 0.2 |

[a] BUFFER (NONE) OR AcA54 (18-25 kD) INHIBITORY FRACTIONS (SEE FIG.1) WERE INCUBATED AT VARIOUS DILUTIONS IN THE PRESENCE OR ABSENCE OF DIFFERENT CONCENTRATIONS OF EITHER hrIL 1α OR hrIL 1β.

[b] [$^3$H]-TdR INCORPORATION IN THYMOCYTES IN THE PRESENCE OF PHA (IL 1/LAF) WAS MEASURED. VALUES REPRESENT MEANS ± SEM (N=3).

FIG. 6  IL 1 INH ACTIVITY MEASURED IN THE IL 1/MCF ASSAY

| FINAL CONCENTRATION OF hrIL-1 (pg/ml) ON HUMAN FIBROBLASTS | FORM OF hrIL-1 ADDED TO THE FIBROBLASTS | FINAL DILUTION OF AcA54 INHIBITORY FRACTION[a] | | | |
|---|---|---|---|---|---|
| | | NONE | 1/20 | 1/40 | 1/80 |
| | | PGE$_2$ PRODUCTION BY HUMAN DERMAL FIBROBLASTS (ng/ml)[b] | | | |
| 0 | – | 0.5 ± 0.1 | 8 ± 3.6 | 8 ± 2.9 | 7 ± 2.0 |
| 20 | α | 20 ± 4.6 | 8 ± 3.5 | 6 ± 2.6 | 10 ± 4.8 |
| | β | 17 ± 3.1 | 12 ± 3.1 | 11 ± 2.0 | 12 ± 5.0 |
| 40 | α | 41 ± 9.6 | 13 ± 4.2 | 10 ± 0.9 | 12 ± 5.1 |
| | β | 28 ± 8.6 | 13 ± 5.8 | 13 ± 3.4 | 6 ± 2.2 |
| 100 | α | 62 ± 11.1 | 8 ± 3.8 | 15 ± 8.2 | 16 ± 2.1 |
| | β | 55 ± 5.2 | 15 ± 6.4 | 21 ± 6.0 | 26 ± 5.1 |
| 2000 | α | 46 ± 3.9 | 49 ± 7.4 | 71 ± 10.2 | 87 ± 11.7 |
| | β | 64 ± 13 | 47 ± 7.0 | 57 ± 39.0 | 113 ± 16.2 |

[a] BUFFER (NONE) OR AcA54 (18-25 kD) INHIBITORY FRACTIONS (SEE FIG.1) WERE INCUBATED AT VARIOUS DILUTIONS IN THE PRESENCE OR ABSENCE OF DIFFERENT CONCENTRATIONS OF EITHER hrIL 1α OR hrIL 1β.
[b] PGE$_2$ PRODUCTION BY CULTURED HUMAN DERMAL FIBROBLASTS WAS MEASURED AFTER 3 DAYS OF CULTURE. VALUES REPRESENT MEANS ± SEM (N=3)

IL 1 INH ACTIVITY MEASURED IN THE IL 1/FIBROBLAST PROLIFERATION ASSAY

| FINAL CONCENTRATION OF hrIL 1 (pg/mL) ON HUMAN DERMAL FIBROBLASTS | FORM OF hrIL 1 ADDED TO THE FIBROBLASTS | FINAL DILUTION OF AcA54 INHIBITORY FRACTION [a] | | | |
|---|---|---|---|---|---|
| | | NONE | 1/20 | 1/40 | 1/80 |
| | | [³H]-TdR INCORPORATION IN HUMAN DERMAL FIBROBLASTS (cpm×10³)[b] | | | |
| 0 | | 1.3 ± 0.4 | 1.2 ± 0.3 | 1.1 ± 0.3 | 1.4 ± 0.4 |
| 20 | α | 2.1 ± 0.4 | 1.1 ± 0.3 | 1.0 ± 0.3 | 1.4 |
| | β | 2.7 ± 0.2 | 1.6 ± 0.1 | 1.3 ± 0.3 | 1.6 |
| 40 | α | 2.5 ± 0.3 | 0.9 ± 0.1 | 1.1 ± 0.4 | 1.1 |
| | β | 3.9 ± 0.2 | 1.3 ± 0.1 | 1.6 ± 0.1 | 2.4 |
| 100 | α | 3.1 ± 0.6 | 1.0 ± 0.3 | 1.4 ± 0.2 | 2.4 |
| | β | 4.0 ± 0.4 | 1.6 ± 0.3 | 2.0 ± 0.2 | 2.7 |
| 250 | α | 4.0 ± 0.6 | 1.6 ± 0.1 | 2.1 ± 0.5 | 3.3 |
| | β | 4.3 ± 0.8 | 1.9 ± 0.2 | 2.4 ± 0.4 | 2.6 |
| 2,000 | α | 3.8 ± 0.5 | 2.8 ± 0.7 | 3.0 ± 0.3 | 4.0 |
| | β | 4.1 ± 0.6 | 2.8 ± 0.4 | 3.4 ± 0.6 | 4.8 |

[a] BUFFER (NONE) OR AcA54 (18-25 kD) INHIBITORY FRACTIONS (SEE FIG. 1) WERE INCUBATED AT VARIOUS DILUTIONS IN THE PRESENCE OR ABSENCE OF DIFFERENT CONCENTRATIONS OF EITHER hrIL 1α OR hrIL 1β.
[b] [³H]-TdR INCORPORATION IN DERMAL FIBROBLASTS IL 1/PROLIFERATION) WAS MEASURED. VALUES REPRESENT MEANS ± SEM (N=3)

FIG. 9

PURIFICATION OF THE IL-1 INHIBITOR

| STEP | PROTEIN | BIOASSAYS ||||| |
|---|---|---|---|---|---|---|---|
| | | IL-1 RECEPTOR BINDING |||| LAF EL-4/CTLL MCF ||
| | | SPECIFIC ACTIVITY | TOTAL ACTIVITY | YIELD | PURIFICATION | SPECIFIC ACTIVITY |||
| | mg | *UNITS/mg | *UNITS x10⁻³ | % | -FOLD | *UNITS/mg |||
| 1 CONCENTRATION URINE | 15190 | 12 | 192 | 100 | 1 | 166 | 32 | 125 |
| 2 QAE-SEPHAROSE | 3350 | 33 | 112 | 58 | 3 | 63 | 27 | 200 |
| 3 DEAE-SEPHAROSE | 480 | 50 | 24 | 13 | 4 | 125 | 40 | 500 |
| 4 AcA 54 (I) | 48 | 454 | 22 | 12 | 37 | 500 | 250 | 540 |
| 5 AcA 54 (II) | 9.3 | 1666 | 16 | 8 | 138 | 526 | 333 | 1110 |
| 6 NEGATIVE-IMMUNO-ABSORPTION | 0.9 | 3334 | 3 | 1.6 | 277 | 2500 | 1250 | 2160 |
| 7 PHENYL-SEPHAROSE | 0.053 | 38461 | 2 | 1 | 3205 | 62500 | 35020 | 30303 |

*UNIT (D₅₀) IS DEFINED AS THE AMOUNT OF IL-1 INHIBITOR (μg) PRODUCING A HALF-MAXIMAL INHIBITION ON THE BIOASSAYS. i.e. IL-1 RECEPTOR BINDING, IL-1/LAF, IL-1/EL-4-CTLL CO-CULTURE AND IL-1/MCF BIOASSAYS.

INTERKEUKIN-1 INHIBITOR

This application is a continuation of application Ser. No. 07/716,787, filed on Jun. 18, 1991 entitled BIOLOGICAL MATERIALS, PROCESSES FOR PRODUCING BIOLOGICAL MATERIALS AND FOR USING SUCH MATERIALS IN THERAPY (now abandoned) which is a continuation of application Ser. No. 07/435,501 filed Jun. 30, 1989 (now abandoned), which is continuation-in-part of application Ser. No. 07/089,632, filed Aug. 26, 1987 (now abandoned.)

TECHNICAL FIELD OF INVENTION

This invention relates to interleukin 1 inhibitors (IL-1 INHs) that selectively inhibit interleukin 1 activity. The invention also relates to processes for purifying such IL-1 INHs from urine and for producing such IL-1 INHs by hosts transformed with recombinant DNA molecules comprising DNA sequences encoding the inhibitors, and to methods of treatment and compositions characterized by such IL-1 INHs. These methods and agents are useful in immunosuppressive and anti-inflammatory applications and therapies.

BACKGROUND ART

Interleukin 1 (IL-1) is a protein cytokine produced primarily by cells of the macrophage/monocyte lineage. There are two distinct IL-1 genes capable of encoding IL-1 polypeptides—IL-1α and IL-1β [P- Auron et al., "Nucleotide Sequence Of Human Monocyte Interleukin-1 Precursor cDNA", *Proc. Natl. Acad. Sci., USA*, 81, p. 7907 (1984); C. March et al., "Cloning, Sequences And Expression Of Two Distinct Human Interleukin 1 Complementary DNA's α and β," *Nature*, 315, p. 641 (1985)]. Studies of their respective biological activities using recombinant IL-1α and β have indicated thus far that both forms of IL-1 share multiple biological activities.

IL-1 has several distinct biological activities. One of these activities—lymphocyte-activating factor (LAF) activity—results in IL-1 being an immunological response mediator and as such, IL-1 stimulates the maturation, differentiation and growth of many cell types, such as immature T and B lymphocytes [P. Auron et al., *Proc. Natl. Acad. Sci. USA*, 81, supra]. Another of IL-1's activities—mononuclear cell factor (MCF) activity—results in IL-1 playing a central role in the regulation of diverse inflammatory responses [C. Dinarello, "An Update of Human Interleukin 1", *J. Clin. Immun.*, 5, p. 287 (1985)] and, as such, IL-1 stimulates several cells, e.g., fibroblasts and chondrocytes, to produce prostaglandin $E_2$ ($PGE_2$) and collagenase, respectively. These responses are involved in the pathogenesis of such joint diseases as rheumatoid arthritis or diseases associated with the destruction of tissue [J. Dayer, "Cytokines and Other Mediators in Rheumatoid Arthritis", *Springer Semin. Immunopath*, 7, p. 387 (1984)]. Further, IL-1 is known to induce the production of IL-2 [J. W. Lowenthal et al. "IL-1 Dependent Induction Of Both IL-2 Secretion and IL-2 Receptor Expression By Thymoma Cells", *J. Imm.*, 137, pp. 1226-1231 (1986)] which is involved in T-cell proliferation. Finally, IL-1 is also known to stimulate molecules on endothelial cells to trap white blood cells [J. Oppenheim et al., "There is More Than One Interleukin 1", *Immun. Today*, 7, p. 45 (1986) ].

It would therefore be of interest to identify and isolate an IL-1 inhibitor which suppresses antigen specific T-cell and B-cell proliferation and suppresses prostaglandin and collagenase synthesis by fibroblasts. Such a compound would be useful for the treatment of disorders involving immune and inflammatory responses. Still further, it would be desirable to isolate an Il-1 inhibitor capable of suppressing IL-1 mediated IL-2 production. It is of further interest to identify a compound that selectively inhibits the activities of IL-1 without concommitantly inhibiting other proteins, e.g., tumor necrosis factors, such as TNF-α, that share several biological properties of IL-1, i.e., $PGE_2$ and collagenase production by human derreal fibroblasts [J. Dayer et al., "Cachectin/Tumor Necrosis Factor Stimulates Collogenase and Prostaglandin $E_2$ Production by Human Synovial Cells and Dermal Fibroblasts", *J. Exp. Med.*, 162, p. 2163 (1985)]or induction of fibroblast proliferation [P. Seckinger et al., "A Urine Inhibitor of Interleukin 1 Activity Affects Both Interleukin 1 α And β But Not Tumor Necrosis Factor α", *J. Immun.* 139, p. 1541 (1987)].

At present, compounds reported as displaying inhibitory effects on IL-1, such as prostaglandins, act primarily as nonselective inhibitors. It has also been reported that urine of febrile patients contains a 20-30 kD selective inhibitor of IL-1 [Z. Liao et al. "Identification Of a Specific Interleukin 1 Inhibitor In The Urine Of Febrile Patients", *J. Exp. Med.*, 159, p. 126 (1984) ]. Liao does not suggest that this compound is other than in very crude form or that it inhibits the MCF activity of IL-1, inhibits the binding of IL-1 to target cell receptors, or inhibits fibroblast proliferation in the presence of IL-1. A second compound reported to have IL-1 inhibitory effects [W. Arend et al., "Effects of Immune Complexes On Production By Human Monocyrtes of Interleukin or an Interleukin 1 Inhibitor", *J. Immun.*, 134, p. 3868 (1985)]is produced by human monocytes cultured on adherent immune complexes. However, the Arend report is ambiguous with respect to whether the compound inhibits both the LAF and MCF activity of IL-1 (see page 3874). In any event, the Arend article does not report that the compound is substantially pure or that it blocks IL-1 binding to target cell receptors or inhibits fibroblast proliferation in the presence of IL-1. A third compound reported to have IL-1 inhibitory effects [J-F. Balavoine et al., "Prostaglandin $E_2$ .And Collagenase Production By Fibroblasts And Synovial Cells Is Regulated By Urine-derived Human Interleukin 1 And Inhibitor(s)", *J. Clin. Invest.* 78, p. 1120 (1986)]is suggested to be in very crude form and its mode of action is not described.

DISCLOSE OF TEE INVENTION

The present invention solves the problems referred to above by providing substantially pure IL-1 inhibitors ("IL-1 INHs") that selectively inhibit IL-1 LAF and IL-1 MCF activities, inhibit IL-1-mediated production of IL-2, inhibit IL-1 mediated fibroblast proliferation and bind to the IL-1 receptors on target cells, for use in immunosuppressive or in anti-inflammatory compositions, methods and therapies. The IL-1 INHs according to this invention do not inhibit TNFα mediated production of $PGE_2$ and collagenase in target cells. The IL-1 INHs of this invention are thus useful in a variety of compositions and methods for immunosuppressive and anti-inflammatory applications. The IL-1 INHs of our invention are characterized as being polypeptides having a molecular weight of approximately 25 kD on SDS/PAGE and an isoelectric point of 4.7 as determined by chromatofocussing.

One embodiment of a process of this invention for producing these IL-1 INHs is purification from natural sources. Such purification comprises the steps of concentrating crude urine of febrile patients, precipitating crude IL-1 INH from the urine and fractionating the IL-1 INH from the other proteins of this precipitate by one or more of ion exchange chromatography, hydrophobic chromatography, gel filtration and immunoabsorption.

A second and preferred embodiment of a process of this invention for producing these IL-1 INHs is the recombinant production of such inhibitors. In such process, DNA sequences that code for the IL-1 INHs of this invention, recombinant DNA molecules characterized by those sequences and various unicellular hosts transformed with those DNA sequences and molecules are employed to produce the IL-1 INHs of this invention (with or without an additional N-terminal methionine ) or portions thereof by fermentation of the transformed hosts. It is to be understood that the IL-1 INH polypeptide according to this invention which displays IL-1 INH activity may include various other amino acid substitutions, additions or deletions to the amino acid sequence of IL-1 INH.

Another object of this invention is to employ the IL-1 INHs of this invention to determine the molecular structures and location of the active IL-1 INH sites and to use that information in designing fragments and peptides for use as IL-1 INHs in the immunosuppressive or anti-inflammatory compositions and methods of this invention.

DETAILED DESCRIPTION OF THE INVENTION

In order that the invention herein described may be fully understood, the following detailed description is set forth.

In the description, the following terms are employed:

MCF—"Mononuclear cell factor". The "MCF activity" of IL-1 defines it ability to stimulate prostaglandin E and collagenase production in numerous target cells, e.g., fibroblasts, synovial cells.

LAF—"Lymphocyte-activating factor". The "LAF activity" of IL-1 defines its ability to stimulate the proliferation and differatiation of T and B lymphocytes.

CTLL—"Cytotoxic T-lymphocyte cell line". CTLL cells are coincubated with EL-4 cells, and used to assay the stimulatory effect of IL-1 on the production of IL-2 from EL-4 cells; the IL-2 then stimulates the proliferation of the CTLL cells which is measurable.

This invention relates to substantially pure IL-1 INHs. "Substantially pure" IL-1 INHs, as defined by this invention, are substantially free of major contaminants, especially apolipoprotein A1 and retinol binding protein, and migrate as a single band on SDS/PAGE.

The IL-1 INHs of this invention selectively inhibit IL-1 LAF and IL-1 MCF activities, inhibit IL-1 mediated IL-2 production by EL-4 cells, inhibit IL-1 mediated fibroblast proliferation and bind to the IL-1 receptors on target cells. Such selective inhibition is defined as having the ability to block IL-1 mediated activity while lacking the ability to block other compounds having some activities similar to IL-1, such as human recombinant TNFα (hrTNFα) which is a mediator of PGE$_2$ and collagenase production. This specificity is an important factor for selectively blocking IL-1 without interfering with the necessary activity of other mediators of the immune system. We demonstrated this specificity of our IL-1 INHs by comparing the effect of the IL-1 INHs of this invention on the activity of IL-1 to hrTNFα, using the IL-1/MCF and fibroblast proliferation assays.

Most preferably, the IL-1 INHs of this invention have a molecular weight of about 25 kD on SDS-PAGE and an isoelectric point of 4.7 as determined by chromatofocussing.

The IL-1 INHs of this invention are capable of inhibiting an IL-1 mediated response in an LAF assay, a MCF assay, an EL-4/cytotoxic T-lymphocyte assay ("EL-4/CTLL") and a fibroblast proliferation assay. In the IL-1/LAF assay, the inhibition of IL-1α or β induced T-cell proliferation is measured by detecting a reduction in level of incorporation of [H$^3$] thymidine in the presence of various dilutions of an IL-1 INH of this invention. In the IL-1/MCF assay the inhibition of IL-1 mediated PGE$_2$ production is measured by a double antibody radioimmunoassay using antiserum to PGE$_2$ in the presence of various dilutions of IL-1 INH of this invention. The decrease of PGE$_2$ into the medium detected by a radioimmunoassay indicates IL-1 INH activity. In the EL-4/CTLL assay the inhibition of IL-1 mediated IL-2 production is measured in the presence of various dilutions of IL-1 INH of this invention. Inhibition is observed as a reduction in the level of uptake of [H$^3$] thymidine ([H$^3$]-TdR ) which is used as a measure of proliferation of CTLL cells. Proliferation only occurs in the presence of IL-1 which induces IL-2 in a dose-dependent manner. In the fibroblast proliferation assay, the inhibition of [H$^3$]-TdR uptake by IL-1 induced fibroblasts is measured in the presence of various dilutions of an IL-1 INH of this invention.

As described above, the IL-1 INHs of this invention specifically bind to IL-1 receptors on target cells. This binding was demonstrated by using a series of IL-1 binding assays. First, we measured the effect of increasing concentrations of IL-1 INH on the binding of labelled IL-1 to receptors on target cells. We observed that higher concentrations of IL-1 INH reduced the amount of bound labelled IL-1. Next, we added an excess of unlabelled IL-1 INH and observed the effect of that excess on the labelled IL-1 bound to a target cell. This assay demonstrated that excess IL-1 INH successfully competed with and replaced the labelled IL-1 bound to the surface of the target cells. We further added an excess of retinol binding protein and observed that this did not prevent the binding of the IL-1 INH to the target cells. This assay demonstrated that our IL-1 INHs compete specifically with IL-1 to bind to the IL-1 receptors on target cells.

This invention also relates to a purification process for isolating an IL-1 INH of this invention from natural sources, e.g., highly febrile patients or AIDS patients suffering from opportunistic infections. This process comprises several steps. In general outline these steps are (1) concentrating urine; (2) precipitating crude IL-1 INH from the concentrated urine and fractionating the IL-1 INH from the other proteins of this precipitate by at least one of ion exchange chromatography, hydrophobic chromatography, gel filtration and immunoabsorption.

In the preferred embodiment of this process, we first concentrate crude urine from febrile patients using standard procedures, e.g., ultrafiltration. We next precipitated a crude fraction containing the IL-1 INH from the concentrated urine pool using ammonium sulfate. After removing the ammonium sulfate by dialysis, we separate the fractions containing the IL-1 INH activity from other proteins using ion exchange chromatography. Specifically, in our most preferred embodiment we employ two anion exchangers—a diethyl-( 2-hydroxypropyl ) aminoethyl-Sepharose column ((QAE)-Sepharose column) and a diethylaminoethyl-Sepharose column ((DEAE)-Sepharose column)—independently or in combination, the DEAE Sepharose column preferably following the QAE Sepharose column. For monitoring the activity of the various fractions, we employed LAF and receptor binding assays. In this embodiment of our invention the IL-1 INH active fractions are next fractionated based on molecular weight using gel filtration, most preferably on a AcA54 gel, again selecting the active fractions as above. The selected fractions are characterized by a molecular weight of about 25kD and by representing at least 90% of the protein content. Principle contaminants are apolipoprotein AI and retinol binding protein. Although these contaminants may be removed in various ways, we prefer to employ monoclonal or polyclonal antibodies raised against apolipoprotein and retinol binding protein by the method of immunoabsorption.

The above IL-1 INH active fractions are further purified by hydrophobic chromatography on a phenyl-Sepharose column which fractionares proteins according to their hydrophobicity. Apolipoprotein A1 and retinol binding protein, for example, are more hydrophobic than proteins of this invention and hence will be retained on the column.

Figure 9:
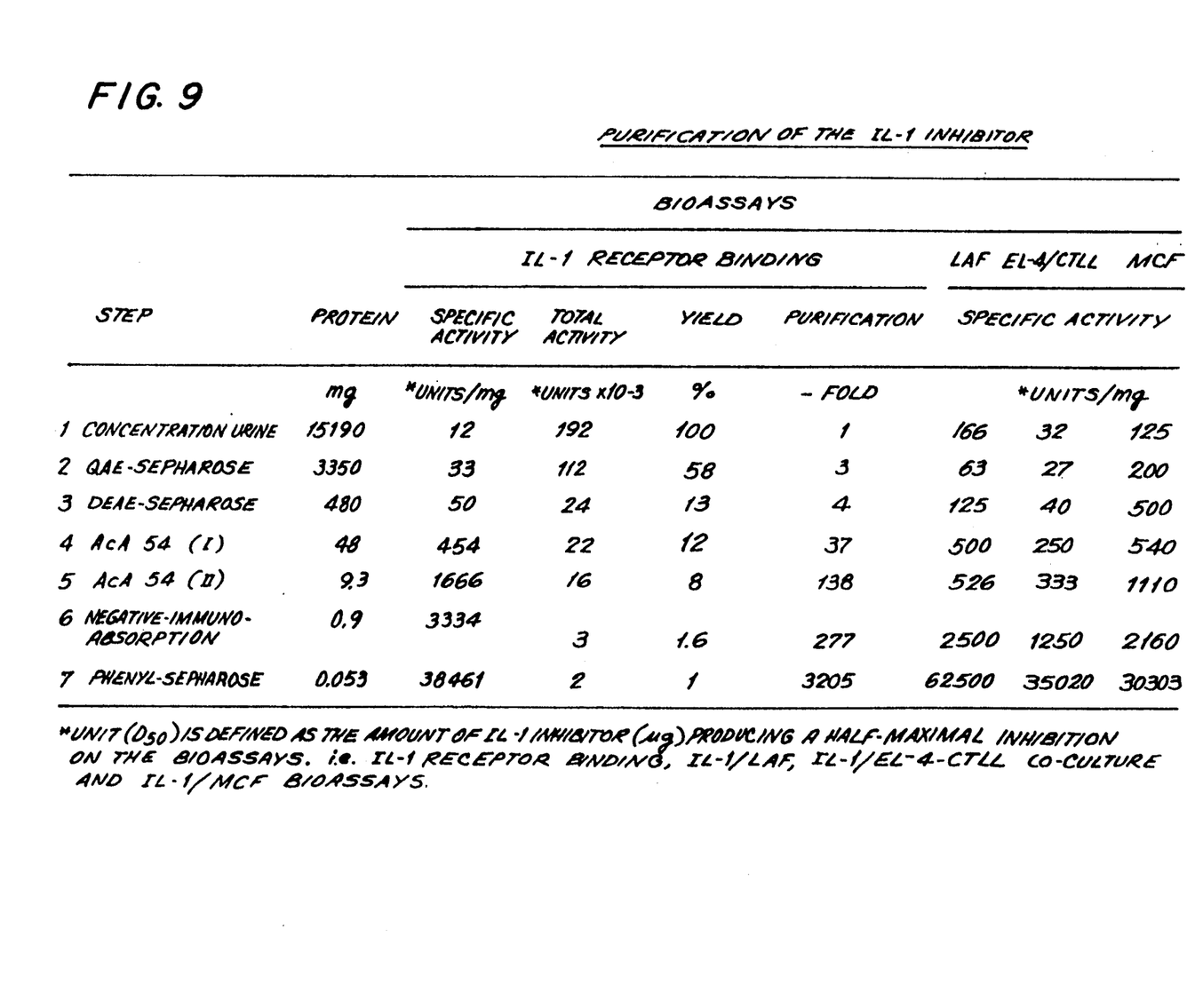
FIG. 9 depicts IL-1 INH specific activity measured after each purification step in the IL-1 receptor binding assay, LAF assay, EL-4/CTLL assay and MCF assay.

Using the above-described preferred process, the specific activity of the IL-1 INH of this invention, i.e., the amount of IL-1 INH required to produce half-maximal inhibition, increased after each purification step. See FIG. 9. We used an IL-1 receptor binding assay, an LAF assay, an EL-4/CTLL assay and a MCF assay to measure this specific activity. However, several other assays could have as well been used.

The IL-1 INH purified in the above process, or preferred process, may be used directly in the immunosuppressive and anti-inflammatory compositions and methods of this invention. However, we prefer to use such purified protein as a source of amino acid sequence data to permit our design of DNA probes for use in isolating and selecting a DNA sequence coding for an IL-1 INH of this invention. Such DNA sequences, recombinant DNA molecules including them, and unicellular hosts transformed with them may then be employed to produce large amounts of the IL-1 INHs of this invention, substantially free from other human proteins, for use in the compositions and therapies of this invention.

More specifically, we determine the amino acid sequences of various portions and fragments of our purified IL-1 INH. We then use those sequences and the DNA sequences deduced as coding for them to design a series of DNA probes potentially useful in screening various DNA libraries for DNA sequences coding for the IL-1 INHs of this invention. Such libraries include chromosomal gene banks and DNA or cDNA libraries prepared from tissue or cell lines that are demonstrated to produce the IL-1 INHs of this invention; such cell lines include monocytic cell lines well known in the art.

As a means for preparing cDNA and finally cloning and expressing IL-1 INH polypeptides, poly A+mRNA is isolated from an IL-1 INH producing cell source, such as stimulated macrophages, using conventional procedures, for example, those described by Land et al., "5-Terminal Sequences Of Eukaryotic mRNA Can Be Cloned With High Efficiency", *Nucleic Acids Research*, 9, pp. 2251–66 (1981); Okayoma and Berg, "High Efficiency Cloning Of Full-Length cDNA, *Mol. and Cell. Biol.*, 2, pp. 161–70 (1982); and Maniatis et al. in "Molecular Cloning" (ed. Cold Spring Harbor Laboratory, Cold Spring Harbor, New York), pp. 229–46 (1982). Next, a cDNA library from the poly A+mRNA isolated above is constructed using conventional procedures, for example, those described by Wickens et al. "Synthesis Of Double-Stranded DNA Complementary To Lysosyme, Ovomucoid And Ovalhuman nRNAs", *J. Biol. Chem.*, 253, pp. 2483–95 (1978); Maniatis et al. in "Molecular Cloning" (ed. Cold Spring Harbor Laboratory, Cold Spring Harbor, New York), pp. 229–46 (1982); and V. Gubler et al. "A Simple And Very Efficient Method For Generating cDNA Libraries", *Gene*, 25, pp. 263–69 (1983).

There are several approaches to screening a library of clones for one containing a particular recombinant DNA molecule, i.e., one containing an IL-1 INH insert. For example, on the basis of a partial amino acid sequence of our purified IL-1 INH, DNA probes that comprise a series of synthetic DNA fragments that code for selected portions of the IL-1 INHs of this invention can be constructed. Techniques for determining amino acid sequences are well known in the art. Having determined the amino acid sequences of various regions of IL-1 INH, pools of degenerate IL-1 INH probes can be chemically synthesized using conventional phosphoamide DNA synthesis techniques for use in screening a variety of DNA libraries to select related DNA sequences by hybridization. The DNA probes are then 5' end-labelled with $^{32}P$ using $^{32}P$-ATP and T4 polynucleotide kinase, substantially as described by A. M. Maxam and W. Gilbert, "A New Method For Sequencing DNA", *Proc. Natl. Acad. Sci. USA*, 74, pp. 560–64 (1977). These DNA probes are then used to screen cDNA or genomic libraries, e.g., cDNA libraries derived from monocylic leukemic cell lines U937, THEP-I and HL60 for DNA sequences that encode IL-1 INHs of this invention using conventional methods. These selected sequences may then be manipulated for the expression of IL-1 INHs in prokaryotic and eukaryotic hosts transformed with them by techniques well known in the art. They are also useful as screening probes to select other related DNA sequences that code for mammalian IL-1 INHs.

The DNA sequences and DNA molecules of the present invention may be expressed using a wide variety of host/vector combinations. For example, useful vectors may consist of segments of chromosomal, non-chromosomal and synthetic DNA sequences, such as various known derivatives of SV40 and known bacterial plasmids, e.g., plasmids from *E. coli* including colE1, pCR1, pBR322, pMB9 and RP4; phage DNAs, e.g., the numerous derivatives of phage, e.g., NM 989, and other DNA phages, e.g. , M13 and other Filamentous single-stranded DNA phages; vectors useful in yeasts, such as the 2$\mu$ plasmid; vectors useful in eukaryotic cells, such as vectors useful in animal cells, such as those containing SV-40 adenovirus and retrovirus derived DNA sequences and and vectors derived from combinations of plasmids and phage DNAs, such as plasmids which have been modified to employ phage DNA or other derivatives thereof.

Such expression vectors are also characterized by at least one expression control sequence that is operatively linked to the IL-1 INH DNA sequence inserted in the vector in order to control and to regulate the expression of that cloned DNA sequence. Examples of useful expression control sequences are the lac system, the trp system, the tac system, the trc system, major operator and promoter regions of phage $\lambda$, the control region of fd coat protein, the glycolytic promoters of yeast, e.g., the promoter for 3-phosphoglycerate kinase, the promoters of yeast acid phosphatase, e.g., Pho5, the promoters of the yeast $\alpha$-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

Among such useful expression vectors are vectors that enable the expression of the cloned IL-1 INH DNA sequences in eukaryotic hosts, such as animal and human cells [e.g., P. J. Southern and P. Berg, *J. Mol. Appl. Genet.*, 1, pp. 327–41 (1982); S. Subramani et al., *Mol. Cell. Biol.*, 1, pp. 854–64 (1981); R. J. Kaufmann and P. A. Sharp, "Amplification And Expression Of Sequences Cotransfected with A Modular Dihydrofolate Reductase Complementary DNA Gene", *J. Mol Biol.*, 159, pp. 601–21 (1982); R. J. Kaufmann and P. A. Sharp, *Mol. Cell. Biol.*, 159, pp. 601–64 (1982) S. I. Scahill et al., "Expression And Characterization Of The Product Of A Human Immune Interferon DNA Gene In Chinese Hamster Ovary Cells", *Proc. Natl. Acad. Sci. U.S.A.*, 80, pp. 4654–59 (1983); G. Urlaub and L. A. Chasin, *Proc. Natl. Acad. Sci. USA*, 77, pp. 4216–20 (1980)].

Furthermore, within each specific expression vector, various sites may be selected for insertion of the IL-1 INH DNA sequences of this invention. These sites are usually designated by the restriction endonuclease which cuts them. They are well recognized by those of skill in the art. It is to be understood that an expression vector useful in this invention need not have a restriction endonuclease site for insertion of the chosen DNA fragment. Instead, the vector could be joined to the fragment by alternative means. The expression vector, and in particular the site chosen therein for insertion of a selected DNA fragment and its operative linking therein to an expression control sequence, is determined by a variety of factors, e.g., number of sites susceptible to a particular restriction enzyme, size of the protein to be expressed, susceptibility of the desired protein to proteolytic degradation by host cell enzymes, contamination or binding of the protein to be expressed by host cell proteins difficult to remove during purification; expression characteristics, such as the location of start and stop codons relative to the vector sequences, and other factors recognized by those of skill in the art. The choice of a vector and an insertion site for a DNA sequence is determined by a balance of these factors, not all selections being equally effective for a given case.

Useful expression hosts include well known eukaryotic and prokaryotic hosts, such as strains of *E. coli*, such as *E. coli* SG-936, *E. coli* HB 101, *E. coli W*3110, *E. coli* X1776, *E. coli* X2282, *E. coli* DHI, and *E. coli* MRC1, *Pseudomonas*, *Bacillus*, such as *Bacillus subtilis*, *Streptomyces*, yeasts and other fungi, animal, such as COS cells and CSO cells, and human cells and plant cells in tissue culture.

Of course, not all host/expression vector combinations function with equal efficiency in expressing the DNA sequences of this invention or in producing the IL-1 INH-like polypeptides of this invention. However, a particular selection of a host/expression vector combination may be made by those of skill in the art after due consideration of the principles set forth herein without departing from the scope of this invention. For example, the selection should be based on a balancing of a number of factors. These include, for example, compatibility of the host and vector, toxicity of the proteins encoded by the DNA sequence to the host, ease of recovery of the desired protein, expression characteristics of the DNA sequences and the expression control sequences operatively linked to them, biosafety, costs and the folding, form or any other necessary post-expression modifications of the desired protein.

The IL-1 INHs produced by fermentation of the prokaryotic and eukaryotic hosts transformed with the DNA sequences of this invention, can then be employed in the immunosuppressive and anti-inflammatory compositions and methods of this invention.

The IL-1 INHs of this invention can also be analyzed to determine their active sites for producing fragments or peptides, including synthetic peptides, having the activity of IL-1 INHs. Among the known techniques for determining such active sites are x-ray crystallography, nuclear magnetic resonance, circular dichroism, UV spectroscopy and site specific mutagenesis. Accordingly, these fragments or peptides are also part of this invention and may be employed in immunosuppressive or anti-inflammatory targets and methods of it.

Administration of the IL-1 INH polypeptides of this invention, or peptides derived or synthesized from them or using their amino acid sequences, or their salts or pharmaceutically acceptable derivatives thereof, may be via any of the conventionally accepted modes of administration of agents which exhibit immunosuppressive or anti-inflammatory activity. These include oral, parenteral, subcutaneous, intravenous, intralesional or topical administration. Local, intralesional or intravenous injection are preferred.

The compositions used in these therapies may also be in a variety of forms. These include, for example, solid, semi-solid and liquid dosage forms, such as tablets, pills, powders, liquid solutions or suspensions, suppositories, injectable and infusable solutions. The preferred form depends on the intended mode of administration and therapeutic application. The compositions also will preferably include conventional pharmaceutically acceptable carriers and may include other medicinal agents, carriers, adjuvants, excipients, etc., e.g., human serum albumin or plasma preparations. Preferably, the compositions of the invention are in the form of a unit dose and will usually be administered one or more times a day.

In order that our invention herein described may be more fully understood, the following examples are set forth. It should be understood that these examples are for illustrative purposes only and should not be construed as limiting this invention in any way to the specific embodiments recited therein.

EXAMPLES

Example 1

Purification of IL-1 INH a) Concentration of Protein From Human Urine

At 4° C., 100 liters of pooled urine from highly febrile patients (>38.5° C.) devoid of urinary infections were concentrated on an Amicon ultrafiltration hollow fiber apparatus to two liters. The resulting solution had a specific activity of 12 U/mg of protein as determined by the IL-1 receptor assay described in Example 2, 166 U/mg of protein as determined by the LAF assay described in Example 3, 32 U/mg of protein as determined by the EL-4/CTLL assay described in Example 4, and 125 U/mg of protein as determined by the MCF assay described in Example 5. A "U" or Unit is defined as the amount of IL-1 INH (μg) which produces half maximal inhibition in each bioassay. See FIG. 9.

b) Precipitation of Protein From Human Urine

We first saturated the concentrated urine pool with solid ammonium sulphate, by adding the ammonium sulphate slowly with constant stirring at 4° C. until we reached an ammonium sulphate saturation of 40%. We next removed the precipitate from the solution by centrifugation in an Sorvall RC-5B (E. I. Du Pont, New Town, Conn.) using a fixed angle GSA rotor at 10000 rpm for 1 hour. We next discarded the pellet and adjusted the supernatant to 80% saturation ammonium sulphate and centrifuged at 10000 rpm for 1 hour. We then resuspended the resultant pellet in 20 mM sodium phosphate (pH 7.2) with 150 mM NaCl (650 ml). We then dialyzed the solution for 24 hrs. against 45 liters (twice) containing 10 mM Tris HCl (pH8), 2 mM EDTA and 5 mM benzamidine HCl to remove the ammonium sulphate.

c) Ion-exchange Chromatography

We next separated the IL-1 INH activity in our combined fraction from other proteins by making use of IL-1 INH's strong binding affinity to two different artion exchangers. Each artion exchanger was employed independently or in combination, the DEAE Sepharose column preferably following the QAE Sepharose column.

1) Diethyl-(2-hydroxypropyl)aminoethyl (QAE) Sepharose Column

Figure 1A:
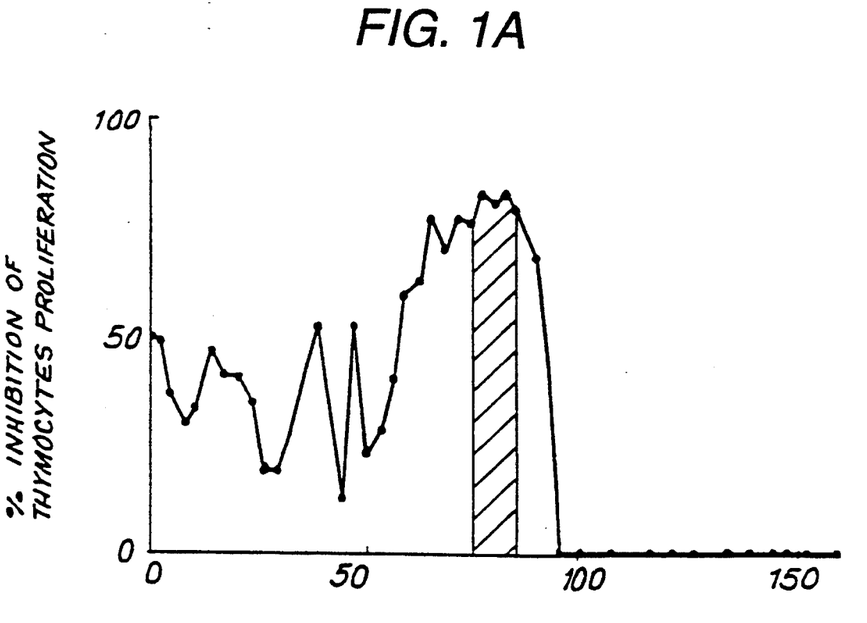
FIGS 1A and 1B depict the activity profile of urinary IL-1 INH obtained from the QAE-Sepharose step.
Figure 1B:
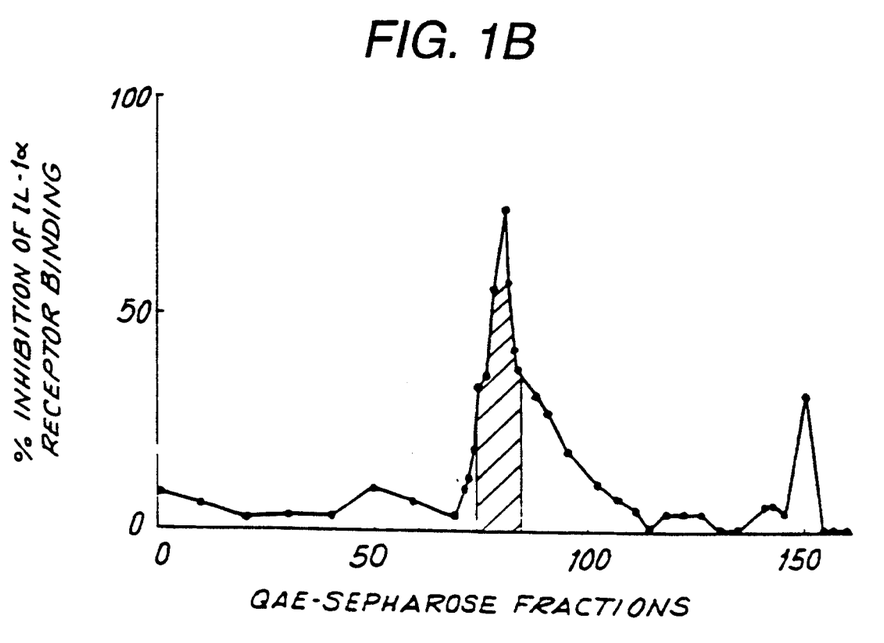

While many anion exchange chromatographic systems are well known to those skilled in the art, we chose to use first a QAE-Sepharose column, 5 cm in diameter X45 cm (Pharmacia Fine Chemicals, Piscataway, New Jersey). After loading the above dialysed solution we washed the column until nonbound proteins were eluted (optical density at 280 nm). We eluted the bound proteins with four column volumes of a salt gradient of 0 to 0.8 M NaCl dissolved in the equilibration buffer. The column-flow was 120 ml/h. We monitored the activity of the various fractions using the LAF and receptor binding assays (infra). See FIG. 1. The fractions displaying the biological activity of IL-1 INH eluted around 150 mM NaCl. The combined active fractions had a specific activity of 33 U/mg of protein as determined by the IL-1 receptor binding assay as described in Example 2, 63 U/mg of protein as determined by the LAF assay as described in Example 3, 27 U/mg of protein as determined by the EL-4/CTLL assay as described in Example 4, and 200 U/mg of protein as determined by the MCF assay as described in Example 5. See FIG. 9.

2) Diethylaminoethyl (DEAE) Sepharose Column

Figure 2A:
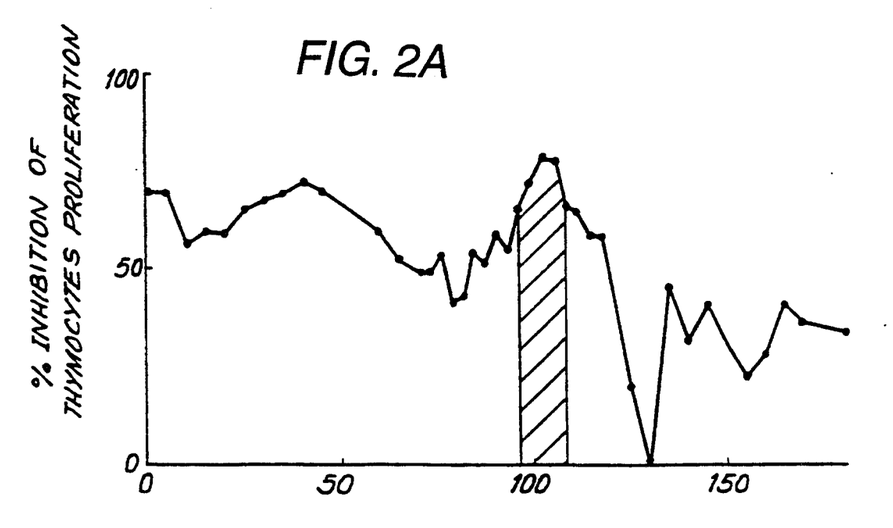
FIGS. 2A and 2B depict the activity profile of urinary IL-1 INH obtained from the DEAE-Sepharose step.
Figure 2B:
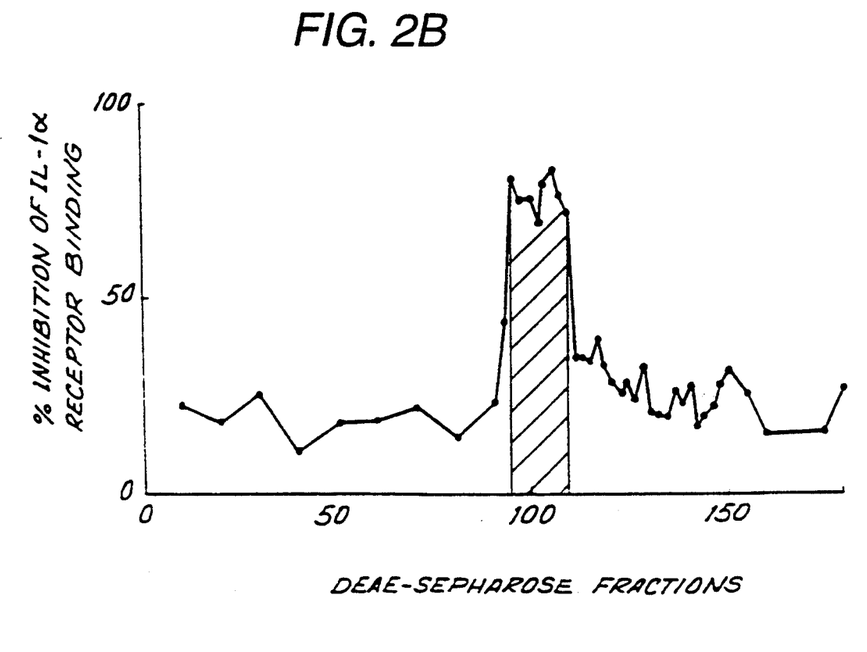

We dialyzed the active pool against 10 mM Tris HCl (pH 7) loaded on a DEAE-Sepharose fast flow column, 2.5 cm X30 cm (Pharmacia Fine Chemicals, Piscataway, New Jersey). The column loaded with the active pool was washed with equilibrium buffer (10 mM Tris HCl, pH 7) until optical density (at 280 nM) was around 0. We then eluted the bound protein with a gradient from 0 to 0.2 M NaCl dissolved in the equilibrium buffer. The gradient was 10 times the volume of the column. The column-flow was 78 ml/h. Again, we monitored the activity of the various fractions as above. This elution afforded elution of the fractions containing IL-1 INH activity at the end of the 90 mM NaCl wash step. FIG. 2 shows the activity profile of urinary IL-1 inhibitor on the DEAE-Sepharose, in which the inhibitory activity was followed on (A) IL-1/LAF assay and (B) IL-1/receptor binding assay (infra).

We next concentrated the active pool to 6 ml by an Areicon ultra filtration apparatus using a YM-10 membrane. The resulting solution had a specific activity of 50 U/mg of protein as determined by the IL-1 receptor binding assay (infra), 125 U/mg of protein as determined by the LAF assay (infra), 40 U/mg of protein as determined by the EL-4/CTLL assay (infra), and 500 U/mg of protein as determined by the MCF assay (infra). See FIG. 9.

It should, of course, be understood that other anion exchange columns could also have been chosen without departing from the scope of this invention.

d) Ultrogel AcA54

Figure 3A:
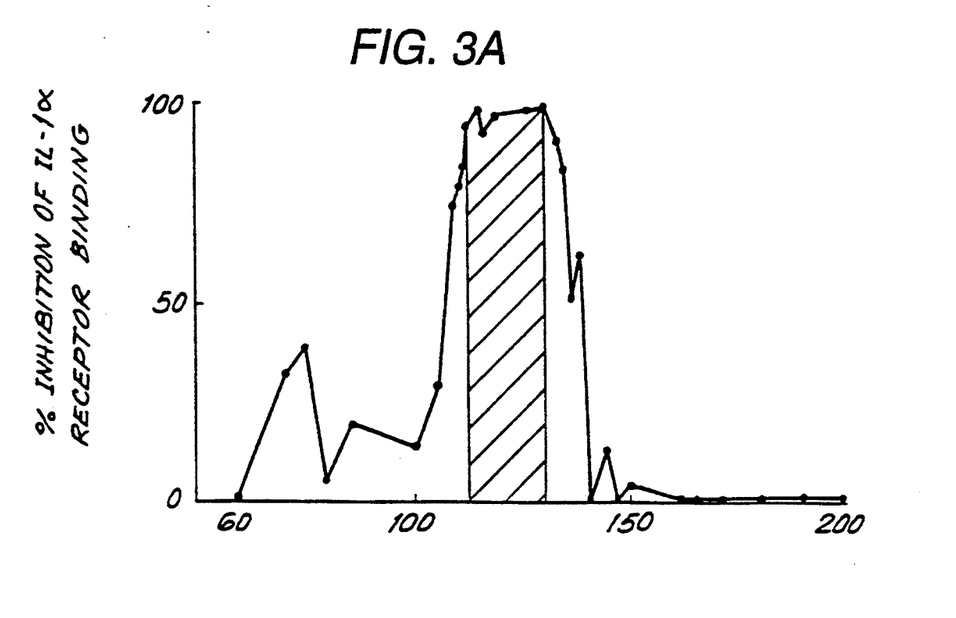
FIGS. 3A and 3B depict the activity profile of the urinary IL-1 INH of the AcA54 filtration fraction.
Figure 3B:
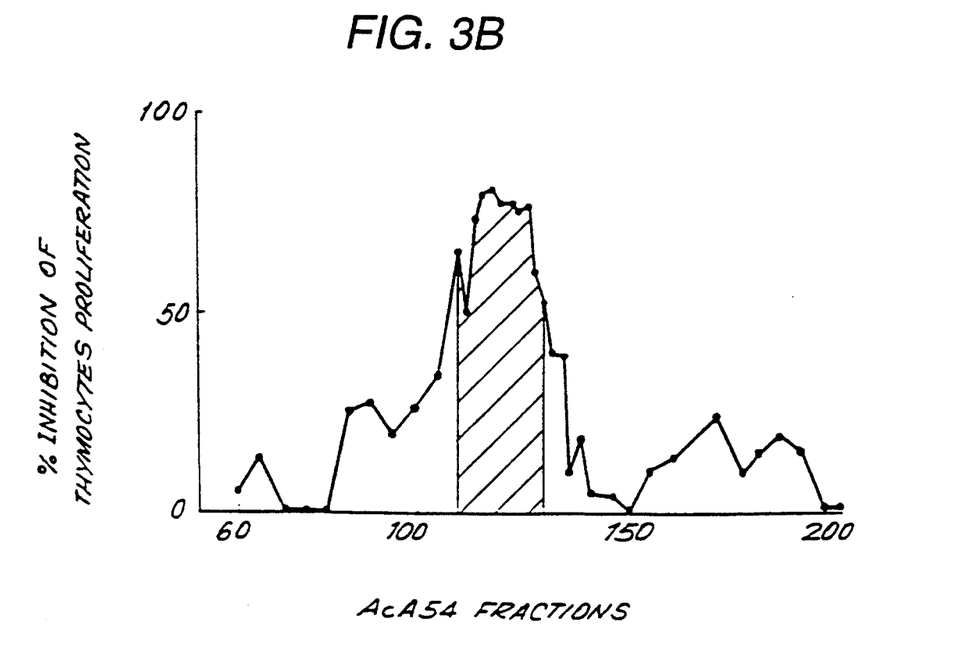

We next fractionated twice the concentrate prepared as described above, according to molecular weight, using gel filtration. While a number of suitable gel filtration systems are well known to those skilled in the art, we chose to use an AcA54 gel (LKB, Sweden) with a fractionation range from 6000–70,000 daltons. Again, we monitored the activity of the fractions as above. See FIG. 3. The resulting pool of the active fractions had a specific activity of 1666 U/mg of protein as determined by an IL-1 receptor binding assay (infra), 526 U/mg of protein as determined by the LAF assay (infra), 333 U/mg of protein as determined by EL-4/CTLL assay (infra), 1110 U/mg of protein as determined by the MCF assay (infra) (see FIG. 9) and a molecular weight of approximately 25 kD. Again, it should be understood that other filtration systems could also have been used.

Figure 4A:
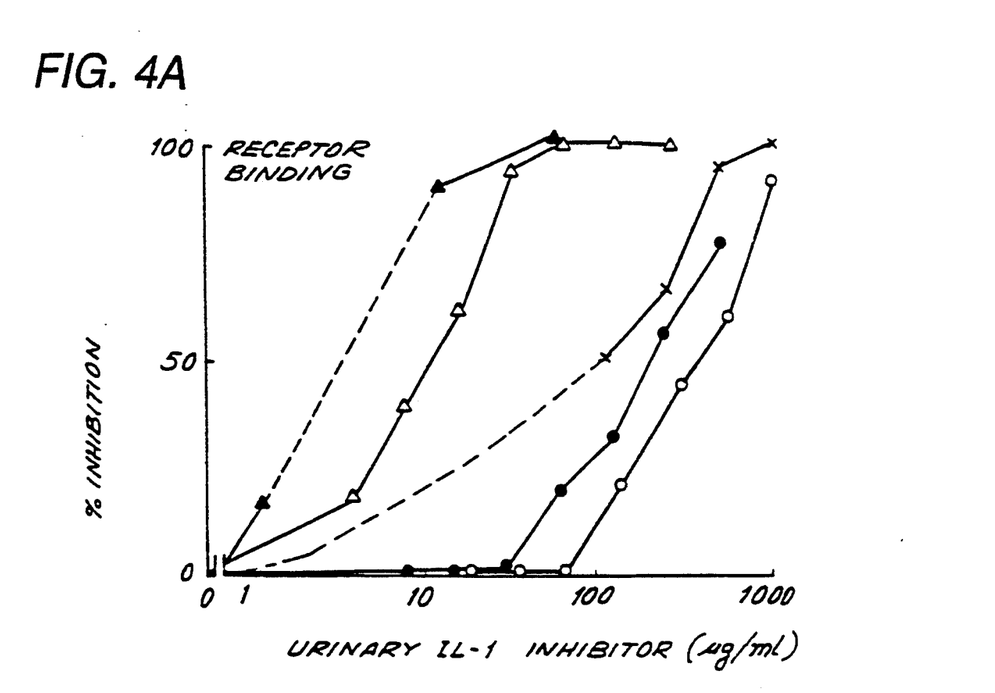
FIGS. 4A and 4B depict the dose-response of the urinary IL-1 INH pools after each purification step measured in IL-1/LAF and IL-1/receptor binding assays.
Figure 4B:
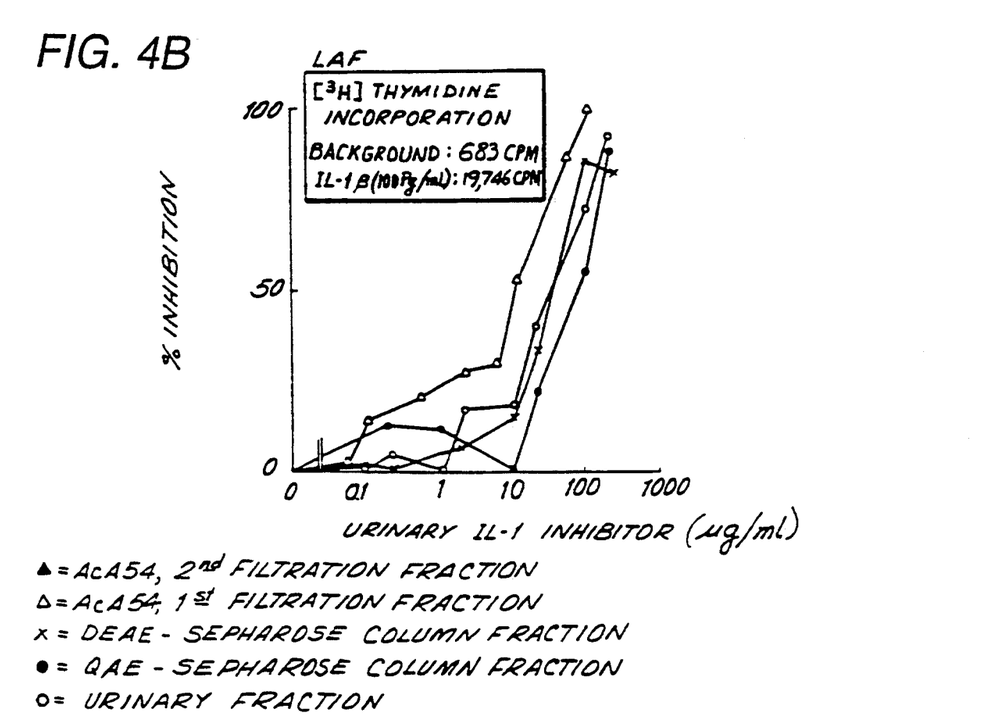

FIG. 4 illustrates the dose-response of the various urinary IL-1 INH pools on the (A) IL-1/LAF assay and (B) IL-1/receptor binding assays described below. After each purification step, i.e., concentrated urine; QAE-Sepharose; DEAE-Sepharose; and AcA54 (twice), the concentration (µg/ml) of IL-1 INH required to achieve inhibition decreased indicating a purer protein.

e) Negative-Immunoabsorption

We analyzed the active pool from the gel filtration by amino acid sequencing, using the conventional method of automated Edman degradation, and observed that the two major contaminants representing at least 90% of the protein content were apolipoprotein AI and retinol binding protein. Although various methods are available to remove these proteins, we chose immunoabsorption and hydrophobic chromatography.

Hence, we next separated out the major contaminants from the IL-1 INH AcA54 active pool by immunoabsorption. Monoclonal and polyclonal antibodies against retinol binding protein and apolipoprotein AI were generated using standard methods of immunization. We then partially purified the immunoglobulin Gs (IgGs) by precipitation with 40% ammonium sulphate saturation. The IgG pellet was resuspended in 0.2 M sodium phosphate and dialyzed against the same buffer. We next coupled the IgG pool to vinylsulfone-activated agarose as described by the manufacturers (KEM-EN-TEC, Biotechnology Corp., Denmark). After equilibrating the immunoabsorbent, with phosphate buffered saline we absorbed the contaminants from the IL-1 INH pool by passing the pool several times over the immunoabsorbant until any retinol binding protein and apolipoprotein AI were completely absorbed as determined by sodium dodecyl sulfate-polyacrylamide gel electrophoresis (SDS-PAGE). The resulting solution had a specific activity of 3334 U/mg of protein as determined by the IL-1 receptor binding assay (infra) 2500 U/mg of protein as determined by the LAF assay (infra) 1250 U/mg of protein as determined by the EL-4/CTLL assay (infra) 2160 U/mg of protein as determined by the MCF assay (infra) (see FIG. 9) and displayed a single peak on SDS/PAGE.

f) Phenyl-Sepharose

The immunoabsorbed IL-1 inhibitor pool was adjusted to 1M NaCl by adding one volume of 2M NaCl dissolved in 10 mM Tris HCl pH 7 and loaded to Phenyl-Sepharose (0.5×5 cm, this resin was obtained from Pharmacia Fine Chemicals Sweden). The resin was previously equilibrated with 10 mM Tris HCl, pH 7, containing 0.2 M NaCl (equilibration buffer). After the loading the column was washed with 3 column volumes of equilibration to elute all the non-bound proteins and the bound proteins were eluted with a gradient from 0.2 M NaCl to 0 M dissolved in 10 mM Tris HCl, pH 7. The total gradient was 50 times the column volume. The column-flow was 30 ml/h. The IL-1 inhibitor activity was eluted around 0.160 M NaCl given a protein of 25 Kda M.W. with a PI of 4.7. The resulting solution had a specific activity of 38461 U/mg of protein as determined by the IL-1 receptor binding assay as described in Example 2, 2,500 U/mg of protein as determined by the LAF assay as described in Example 3, 35,020 U/mg of protein as determined by the EL-4/CTLL assay as described in Example 4, 30,303 U/mg of protein as determined by the MCF assay as described in Example 5 (see FIG. 9) and displayed a single peak on SDS/page.

Example 2

Receptor Binding Ability of IL-1 INH

To determine the binding characteristics of our IL-1 INH to the IL-1 receptor on EL-4-6.1 target cells, we first tested to see if IL-1 INH interfered with the binding of [$^{125}$I]-IL-1 to the target cells. We labeled IL-1 with $^{125}$I by the Chloramine T method [Lowenthal et al., "Binding and Internalization of Interleukin-1 by T Cells,"*J. Exp. Med.*, 164, p. 1060]and coincubated it with an excess of unlabeled IL-1 INH, followed by washing on an oil gradient. Using a gamma counter, we next measured the retained material with the cells and found that increasing the concentration of IL-1 INH reduced the amount of [$^{125}$I]-IL-1 bound to the surface of the target cells.

We further tested to see if IL-1 INH interfered with the binding of [$^{125}$I]-IL-1 INH to the target cells, whether binding of [$^{125}$I]-IL-! INH could be competed by unlabeled IL-1 or whether binding of [$^{125}$I]-IL-1 INH to the target cells could be competed with retinol binding protein or apolipoprotein AI. With [$^{125}$I], we labeled IL-1 INH by the method of Bolton and Hunter [Bolton and Hunter "The labelling Of Proteins To High specific Radioactivities By conjugation to a $^{125}$I-Containing Acylating Agent," *Biochem. J.*, 133, p. 529 (1973)]. Incubation of the material with EL-4-6.1 target cells followed by washing on an oil gradient, and analyzing on SDS PAGE showed that a species of approximately 25 kD binds to the EL-4 cells. We observed the coincubation of the [$^{125}$I]-IL-1 INH with an excess of unlabeled IL-1 INH prevented the binding of the labeled 25 kD species. We also coincubated the [$^{125}$I]-IL-1-INH with 50 nanograms of unlabeled IL-1β and found this prevented the binding of the labeled 25 kD species. We also coincubated the [$^{125}$I]-IL-1 INH with 1 µg of immunopurified retinol binding protein and with 1 µg of recombinant apolipoprotein AI and found that this did not prevent the binding of the labeled 25 kD species. Thus the 25 kD species present in the labeled IL-1 INH preparation binds to the surface of intact EL-4-6.1 cells, and this binding is competed by unlabeled inhibitor and by IL-1, but not by retinol binding protein or apolipoprotein AI.

Example 3

IL-1/LAF Assay

Figure 5:
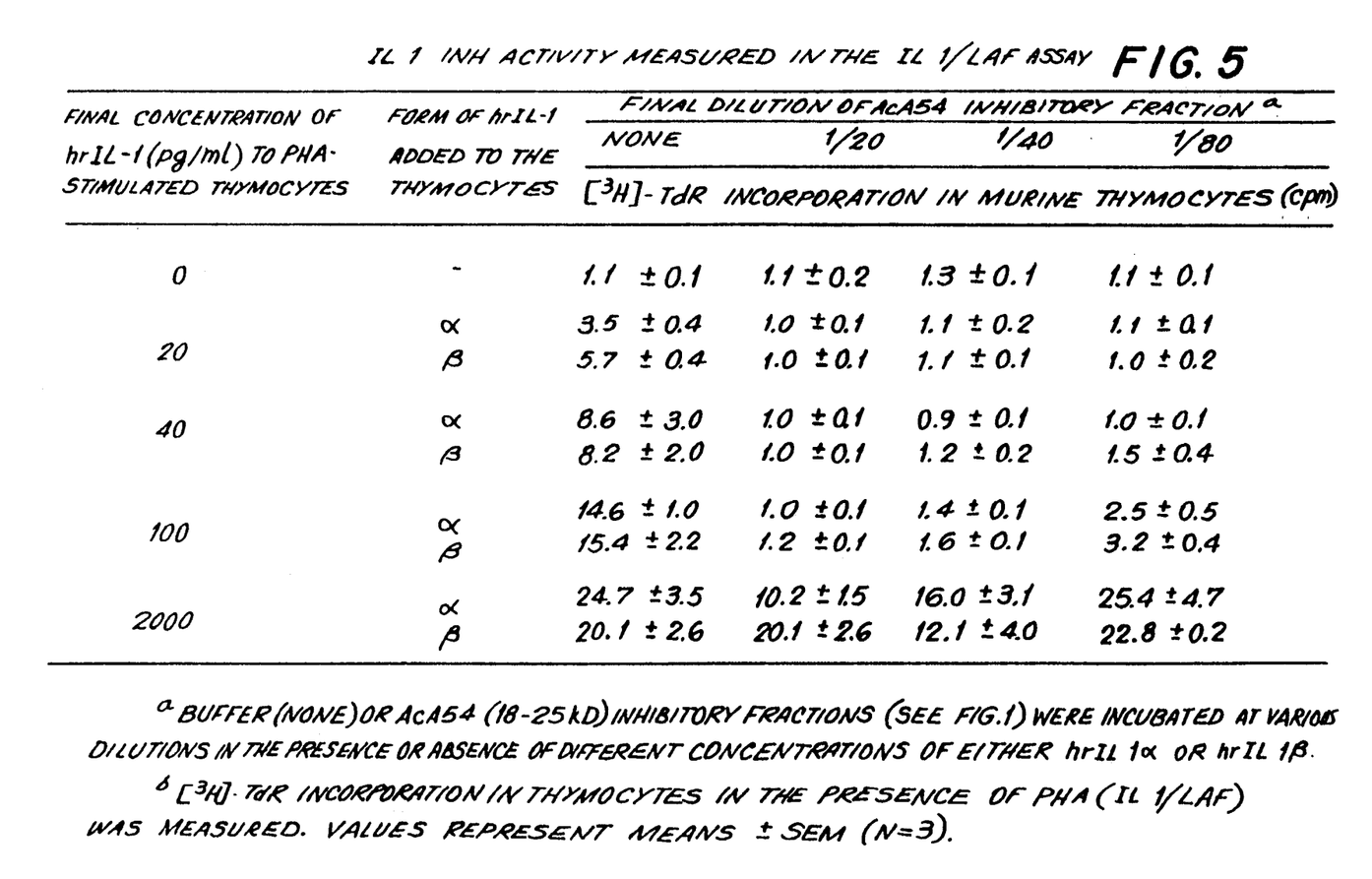
FIG. 5 depicts the IL-1 INH activity measured in the IL-1/LAF assay.

We demonstrated the inhibitory activity of IL-1 INH in a IL-1/LAF assay, as measured by thymocyte (T-cell) proliferation in the C$_3$H/HeJ mouse [J. M. Dayer et al., "Human Recombinant IL-1 Stimulates Collagenase And Prostaglandin E2 Production By Human Synovial Cells", *J. Clin Invest.*, 77, p. 645 (1986)]. We costimulated the thymocyte cells for 72 hours with PHA (1 µg/ml) in the presence of either hrIL-1α [P. Wingfield et al., "Purification and Characterization Of Human Interleukin-1 Expressed In *E. coli.*" *Eur. J. Biochem*, 165, p. 537 (1987)]or IL-1β [P. Wingfield et al., "Purification And Characterization Of Human Interleukin-1β Expressed In Recombinant *E. coli*", *Eur. J. Biochem*, 160, p. 491 (1986) ]at different final concentrations ranging from 20 pg/ml to 2,000 pg/ml of hrIL-1 as shown in FIG. 5. We obtained complete inhibition of the costimulated hIL-1α or hIL-1β thymocyte proliferation when we added the IL-1 INH fractions from example 1 (e) to the cells. Inhibitory activity was monitored at three dilutions of IL-1 INH:1/20, 1/40 and 1/80.

Since addition of IL-1 INH to PEA-stimulated cells, in the absence of hrIL-1 did not affect [$H^3$]-TdR incorporation, we determined that inhibition was not due to a cytotoxic or non-specific effect but to inhibition of IL-1 biological activity.

Example 4

EL-4/CTLL Assay

We determined IL-1 INH's inhibitory activity by observing whether IL-1α's or IL-1β's ability to induce production of IL-2 in EL-4 cells could be inhibited [see, e.g., A. J. H. Gearing et al., "A Simple Sensitive Bioassay For IL-1 Which is Unresponsive to $10^3$ U/ml Of IL-2", *J. Immun. Met.*, 99, p. 7 (1987) ]. This is measured by co-culturing a subclone of EL-4 cells unable to take-up thymidine from surrounding medium with CTLL-2 cells and observing whether the CTLL-2 cells proliferate.

EL-4.6.1 c10 cells and CTLL-2 cells were cultured together at a concentration of $10^4$ cells of each type per microtiter well (96 well plate) in the presence of IL-1α or IL-1β at about 1 picogram/ml, together with IL-1 INH from Example 1(e). We added 1 microCurie of [$H^3$[-TdR after 18 hrs. of co-culture and incubated for an additional 6 hours at 37° C. in a humidired atmosphere. Cells were harvested on a MASH cell harvester onto glass fiber strips, dried and prepared with scintillation cocktail for counting in a beta counter. We obtained complet inhibition of [$H^3$]-TdR incorporation at IL-1 INH dilutions of 1/20, 1/40 and 1/80.

Example 5

IL-1/MCF Assay

Figure 6:
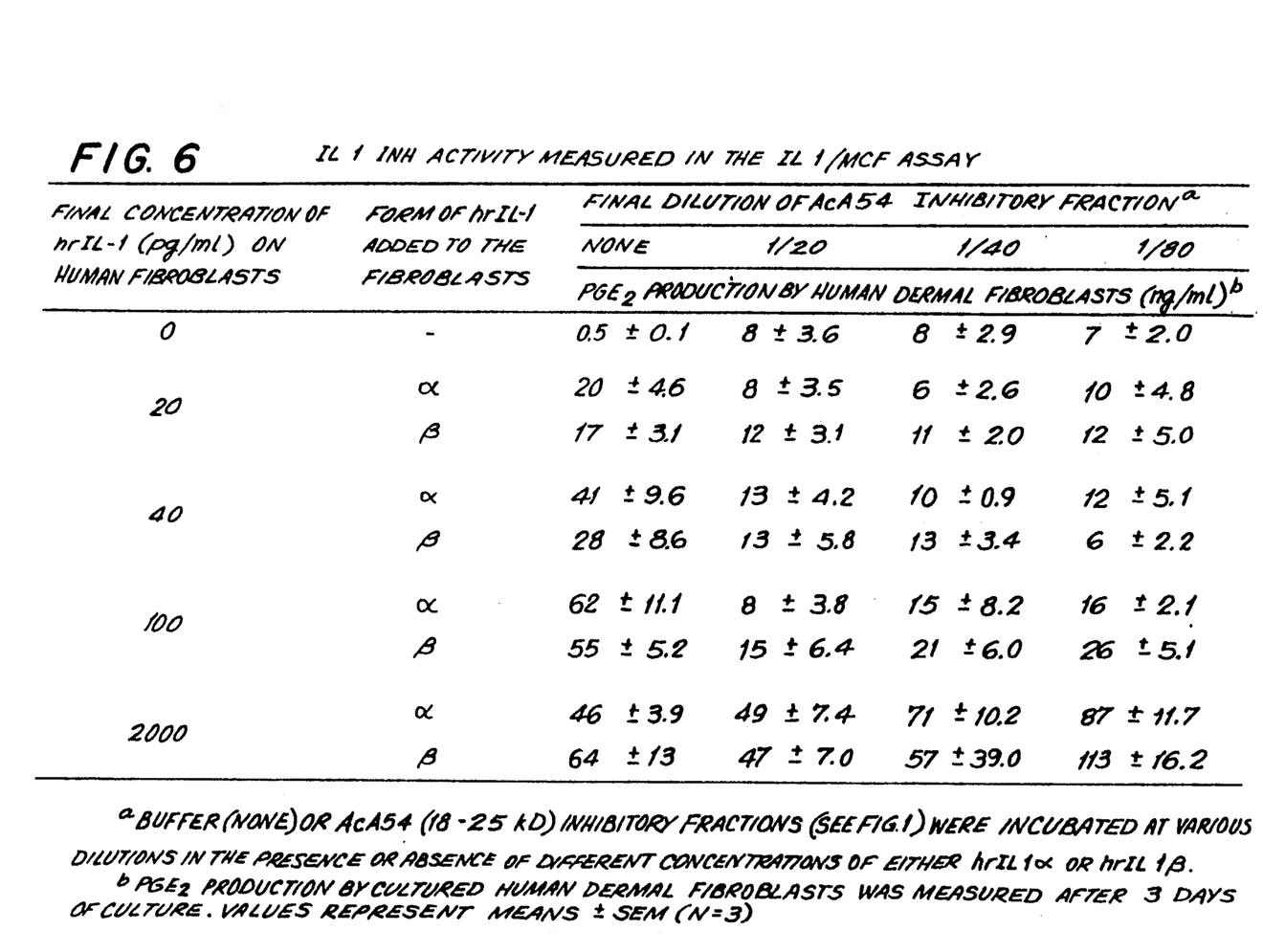
FIG. 6 depicts IL-1 INH activity measured in the IL-1/MCF assay.

We further demonstrated the inhibitory activity of IL-1 INH in a IL-1/MCF assay as measured on fibroblasts obtained from human infant foreskin J. Dayer et al., "Participation Of Monocyte-Macrophage And Lymphocyte In The Production Of A Factor That Stimulates Collagenase And Prostaglandin Release By Rheumatoid Synovial Cells," *J. Clin. Invest.*, 64, p. 1386 (1979); J. Dayer et al. "Induction Of Human Interleukin-1 mRNA Measured By Collagenase And Prostaglandin E2-Stimulating Activity In Rheumatoid Synovial Cells," *Eur. J. Immunol.*, 14, p. 898 (1984)]. We stimulated the fibroblasts with hrIL-1α or hrIL-1β at the same concentrations as in the IL-1/LAF assay, and monitored the inhibitory activity at the same final dilutions of IL-1 INH as in the IL-1/LAF assay. After we cultured the cells for 72 hours, we measured the prostaglandin E2 production in fibroblast supernatants by a double antibody radioimmunoassay [J. Dayer (1979), supra] using an antiserum to prostaglandin $E_2$. As shown in FIG. 6, we observed a dose response of prostaglandin E2 production up to concentrations of 100 pg/ml by either hrIL-1α or hrIL-1β. We were able to inhibit this biological activity by adding the IL-1 INH fractions from Example 1 ( e ). We determined that IL-1 INH was again effective against hrIL-1α and hrIL-1β.

Figure 7:
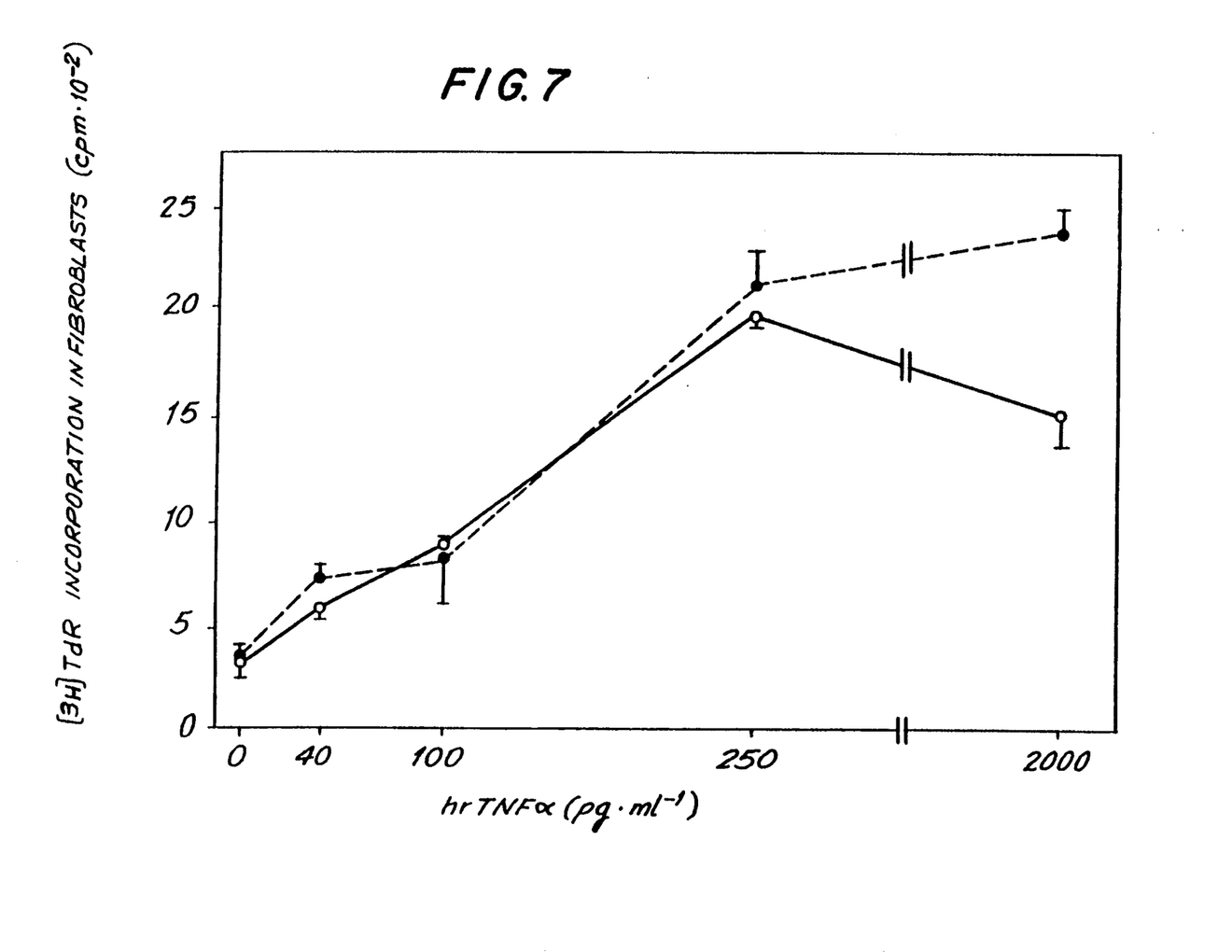
FIG. 7 depicts that IL-1 INH does not affect hrTNFα-induced PGE$_2$ production.

We then performed the above assay substituting hrTNFα [A. Marmenout et al., "Molecular Cloning and Expression of TNF And Comparison With Mouse TNF", *Eur. J. Biochem,* 152, pp. 515–22 (1985)]for hrIL-1 to determine the specificity of IL-1 INH, since TNFα is also a mediator of protaglandin E2 and collagenase production. As shown in FIG. 7, hrTNF -induced prostaglandin $E_2$ production was not significantly affected by addition of our IL-1 INH, illustrating the specificity of our IL-1 INH.

Example 6

Fibroblast Proliferation Assay

Figure 8:
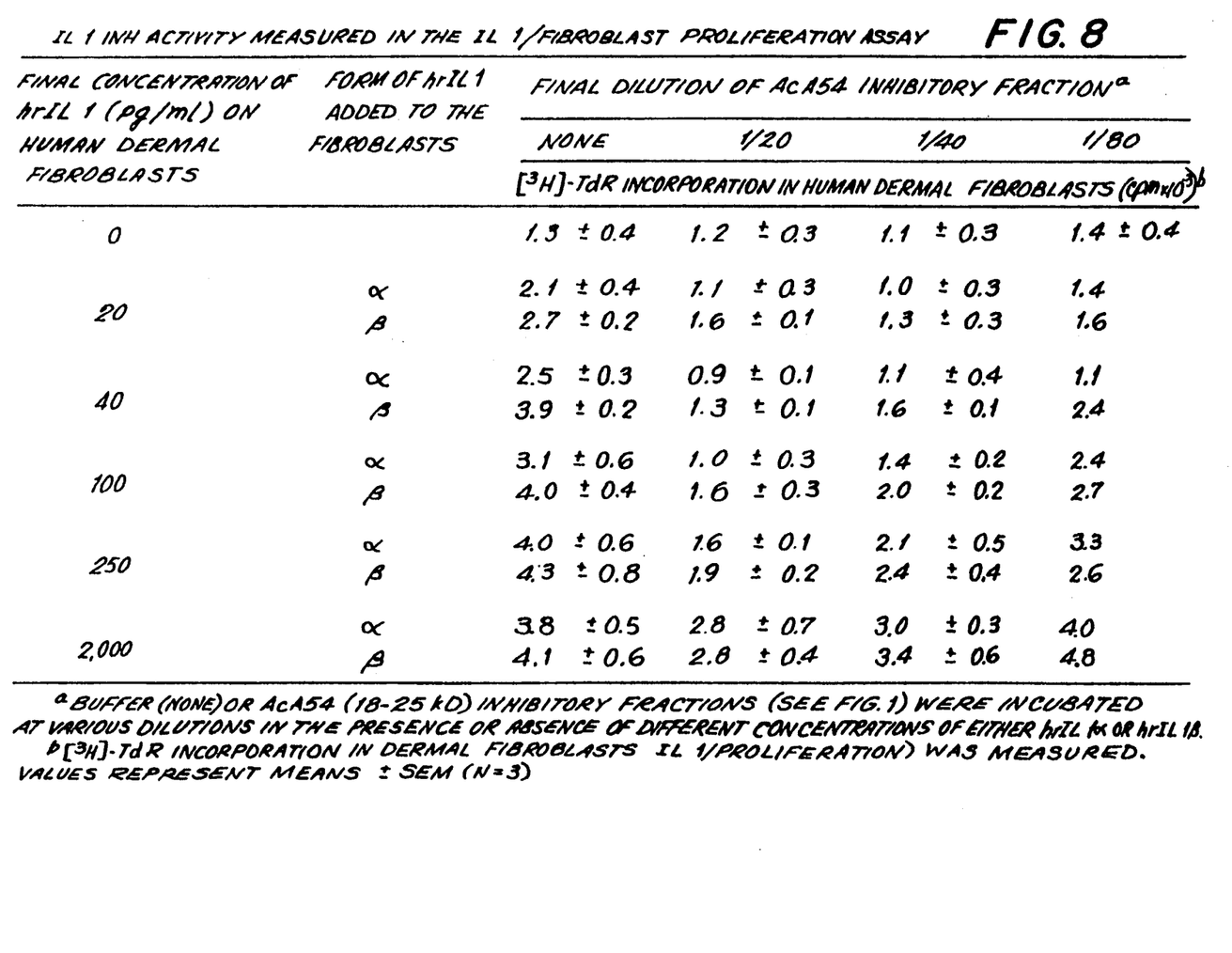
FIG. 8 depicts IL-1 INH activity measured in the IL-1/fibroblast proliferation assay.

We further assayed IL-1's biological activity in the presence of the IL-1 INH from Example 1(e) using a fibroblast proliferation assay, measured by [$H^3$]-TdR incorporation. After culturing human foreskin fibroblasts in Eagle's MEM supplemented with 10 mM HEPES, penicillin 100 U/ml, streptomycin 100 ug/ml, 1% glutamine, 1% non-essential amino acids and 2% FCS, we seeded the cells in 96-well plates (2000 cells/well) and cultured for 24 hours in a 5% $CO_2$ incubator at 37° C. After removing the medium we stimulated the fibroblast cells by adding either hrIL-1α or hrIL-1β and added IL-1 INH at the same dilutions as the above assays. We waited 48 hours and the pulsed the cells with [$H^3$]-TdR for a further 16 hours. Medium was removed from the cells which were then washed with PBS and trypsinized at 37° C. for 15 additional minutes. With a cell harvester (Skatron, Lief, Norway) we collected the cells onto glass filters (Skatron, Inc., Sterling, Virginia, U.S.A.) washed with water, air dried and determined the cpm incorporation using a scintillation counter. As shown in FIG. 8, fibroblast proliferation was dose-dependent for hrIL-1α and hrIL-1β. We obtained maximal [$H^3$]-TdR incorporation with 250 pg/ml of hrIL-1α or β. Addition of the AcA54 inhibitory fraction resulted also in a complete decrease of hrIL-1-induced proliferation. We also achieved complete reversibility of inhibition by increasing IL-1 concentrations or by diluting the IL-1 INH.

We also determined the specificity of this inhibition by stimulating the fibroblasts with hrTNFα, which induces fibroblast proliferation in a dose-dependent fashion up to concentrations of 250 pg/ml. Our addition of the AcA54 inhibitory fraction did not result in the inhibition of hrTNFα bioactivity. This confirms the specificity of the IL-1 INH.

Example 7

Determination Of The Isoelectric Point

We used the pool of protein eluted from Example 1(e) to load on a PBE 94 chromatofocusing (Pharmacia Fine Chemical, Sweden) column (2.5×10 cm) previously equilibrated with 25 mM imidazole (pH 7.5). We added a polybuffer 74 HCl, pH 4, which afforded elution of bound proteins, depending on their isoelectric points. We determined that the pI of the IL-1 INH is 4.7.

While we have hereinbefore described a number of embodiments of this invention, it is apparent that our basic constructions can be altered to provide other embodiments which utilize the processes and compositions of this invention.

Therefore, it will be appreciated that the scope of this invention is to be defined by the claims appended hereto rather than the specific embodiments which we have presented by way of example.

We claim:

1. A substantially pure IL-1 INH, migrating as a single band on SDS/PAGE and substantially free of apolipoprotein Al and retinol binding protein, the IL-1 INH being characterized by an inhibitory activity to (1) the LAF activity of IL-1
(2) the MCF activity of IL-1,
(3) the IL-1 mediated fibroblast proliferation, and
(4) the IL-1 binding to IL-1 receptors, and non-inhibitory activity to the TNFα mediated production of $PGE_2$ and collagenase, wherein the IL-1 INH has a specific activity of at least $1.2 \times 10^3$ U/mg in an IL-1 mediated IL-2 production assay.

2. The IL-1 INH according to claim 1 wherein IL-1 INH is further characterized by an inhibitory activity to IL-1-mediated production of IL-2.

3. The IL-1 INH according to claim 1, wherein the IL-1 INH specifically binds to IL-1 receptors on target cells.

4. The IL-1 INH according to claim 1 wherein the IL-1 INH has a molecular weight of about 25,000 daltons on SDS PAGE.

5. The IL-1 INH according to claim 4, wherein the IL-1 INH has an isoelectric point of 4.7 by chromatofocussing.

6. The IL-1 INH according to any one of claims 1–5 wherein the IL-INH is substantially free from other proteins.

7. The IL-1 INH according to claim 1 wherein the IL-1 INH has a specific activity of at least $1.2 \times 10^3$ U/mg in an EL-4/CTLL assay.

8. The IL-1 INH according to claim 1, wherein the IL-1 INH has a specific activity of at least $3.8 \times 10^4$ U/mg in an IL-1 receptor binding assay.

9. The IL-1 INH according to claim 1, wherein the IL-1 INH has a specific activity of at least $6.2 \times 10^4$ U/mg in an IL-1/LAF assay.

10. The IL-1 INH according to claim 1, wherein the IL-1 INH has a specific activity of at least $3.5 \times 10^4$ U/mg in an EL-4/CTLL assay.

11. The IL-1 INH according to claim 1, wherein the IL-1 INH has a specific activity of at least $3.0 \times 10^4$ U/mg in an IL-1/MCF assay.

12. A pharmaceutical composition comprising a therapeutically effective amount of an IL-1 INH according to any one of claims 1 to 5 or 7–11 in a pharmaceutically acceptable vehicle.

* * * * *